US005576833A

United States Patent [19]
Miyoshi et al.

[11] Patent Number: 5,576,833
[45] Date of Patent: Nov. 19, 1996

[54] WAFER PATTERN DEFECT DETECTION METHOD AND APPARATUS THEREFOR

[75] Inventors: Motosuke Miyoshi; Yuichiro Yamazaki, both of Tokyo-To, Japan

[73] Assignee: Kabushiki Kaisha Toshiba, Kawasaki, Japan

[21] Appl. No.: 402,486

[22] Filed: Mar. 10, 1995

[30] Foreign Application Priority Data

Mar. 11, 1994 [JP] Japan .................................. 6-041346

[51] Int. Cl.⁶ .................................................. G01B 11/00
[52] U.S. Cl. .......................... 356/394; 356/357; 356/389; 356/237; 356/431
[58] Field of Search ..................... 356/394, 357, 356/350, 548, 388, 389, 237, 430, 431; 250/207, 214 VT

[56] References Cited

U.S. PATENT DOCUMENTS 4,294,544  10/1981  Altschuler et al. ....................... 356/76
5,159,231  10/1992  Feller et al. .......................... 313/103 CM

FOREIGN PATENT DOCUMENTS

6-111742  4/1994  Japan .

Primary Examiner—Frank Gonzalez
Assistant Examiner—Reginald A. Ratliff
Attorney, Agent, or Firm—Oblon, Spivak, McClelland, Maier & Neustadt, P.C.

[57] ABSTRACT

A scanning electron beam is formed as a rectangular electron beam. The electro-optical system which forms this rectangular beam has a rectangular-cathode light source and a quadrupole lens system. This rectangular beam is scanned in its short-axis (X-axis) direction by a deflection system while a stage is moved in its long-axis (Y-axis) direction to achieve scanning of the surface of the wafer under inspection. The rectangular beam corresponds to a number of circular beams arranged in a row. Therefore, pixel signals corresponding to a number of pixels equal to the aspect ratio of the rectangular beam (ratio of the length in the long-axis direction to the length in the short-axis direction) are simultaneously output.

11 Claims, 10 Drawing Sheets

WAFER PATTERN DEFECT DETECTION METHOD AND APPARATUS THEREFOR

BACKGROUND OF THE INVENTION

1. Field of Utilization in Industry

The present invention relates to a wafer defect detection method and apparatus therefor, this method making use of an electron beam to perform high-sensitivity and high-speed detection of defects in the pattern formed on a wafer, and the apparatus having a configuration for the purpose of performing this detection. More specifically, the present invention relates to a method whereby an electron beam scans over the pattern, the secondary electron image or reflected electron image resulting from this scanning being compared while scanning to detect the existence or non-existence of defects, this method performing high-speed detection, while maintaining high sensitivity and detection reliability (capture rate).

2. Description of the Background Art

In the development of VLSI processes or manufacture of VLSI devices, the most basic method and essential technology for improving yield is to detect pattern defects, and to determine the cause of such defects. The dimensions of defects which are to be detected are established by the minimum dimensions of the pattern, and in general it is necessary to detect defects that are ½ of the minimum pattern dimension or smaller. This means that in the future there will be a need to have detection sensitivity of 0.2 µm in the case of a 64M DRAM having a minimum pattern dimension of 0.4 µm, and a detection sensitivity of 0.1 µm in the case of a 256M DRAM having a minimum pattern dimension of 0.25 µm. In fields requiring such defect detection sensitivities, it is necessary to use an electron beam. This is because the defects which must be detected are smaller than the minimum resolution obtainable using an electron microscope and obtained using light.

Next, the method of using an electron beam for detection of defects will be described as it was practiced in the prior art. This method can be generally divided into its constituent parts of image capture processing and defect detection processing, with defect detection for the purpose of fault analysis generally making use of pattern comparison. That comparison takes the form of comparing two images, one from the pattern being inspected for defects and other from the pattern of another wafer having the same pattern. If the patterns are the same, the pattern under inspection is judged to be good. If there is a difference between the pattern images, the judgment is made that there exists a defect in the pattern being inspected.

In making this comparison, the most common method is to make a comparison a pair of the patterns of dies (chips) which are arranged on both the wafers from the same area (observation screen) of each wafer, this method being known as the die-to-die method.

In the case of memory cells, in which the same patterns are line up on the wafer, the scanning proceeds sequentially as comparisons are made between adjacent patterns. Because this method compares adjacent patterns, it has a simpler scanning method and can be done faster than the die-to-die method, and there has been a recent trend towards the widespread use of this method. A slightly more detailed description of the beam scanning method and the signal detection method used in this method will be presented next (P. Sandland et al, J. Vac. Sci. Technol., B9(6), Nov/Dec, p. 3005, 1991).

Figure 1:
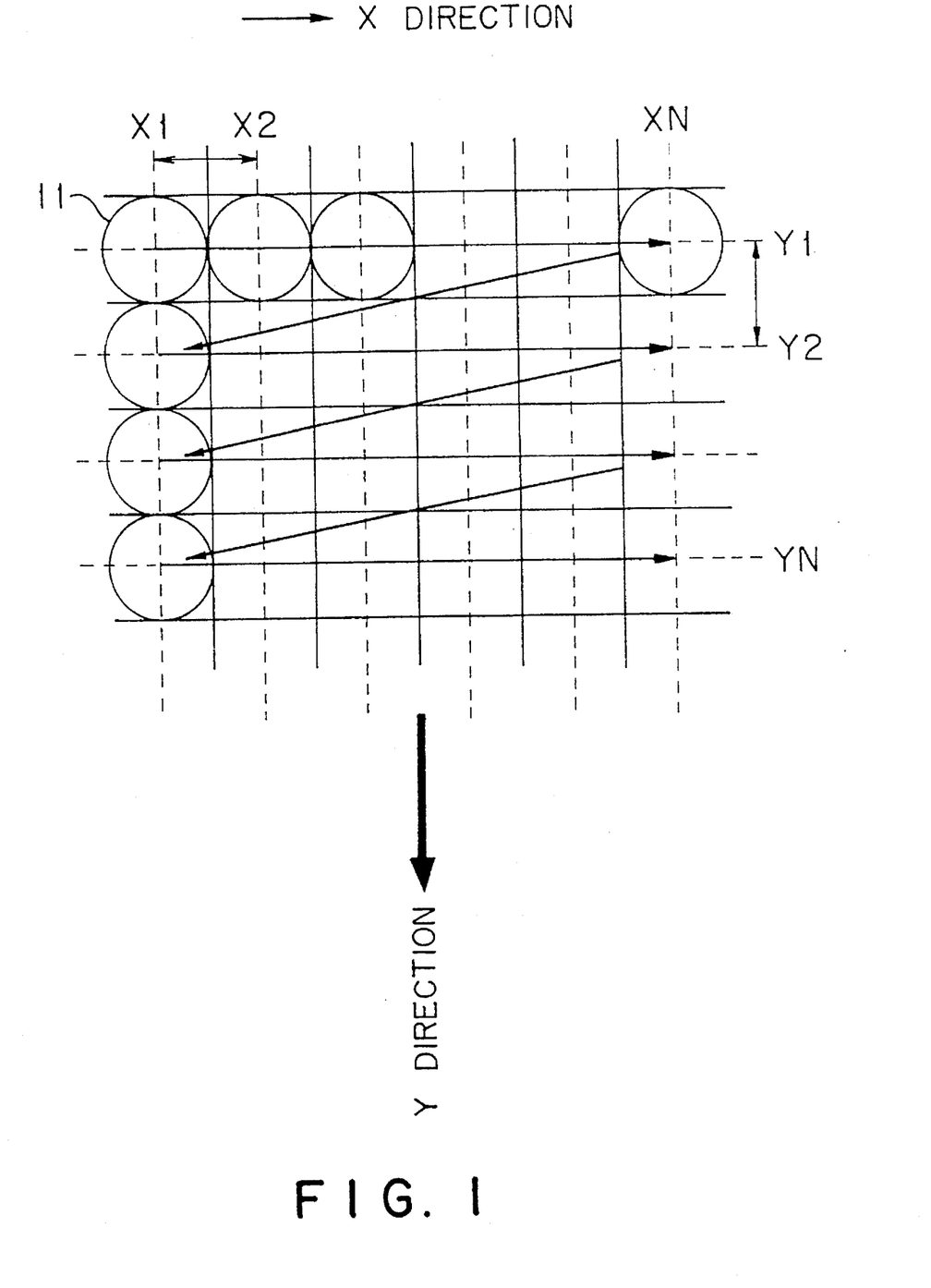
FIG. 1 is a drawing which shows the method of scanning by means of a circular beam in the prior art.
Figure 2:
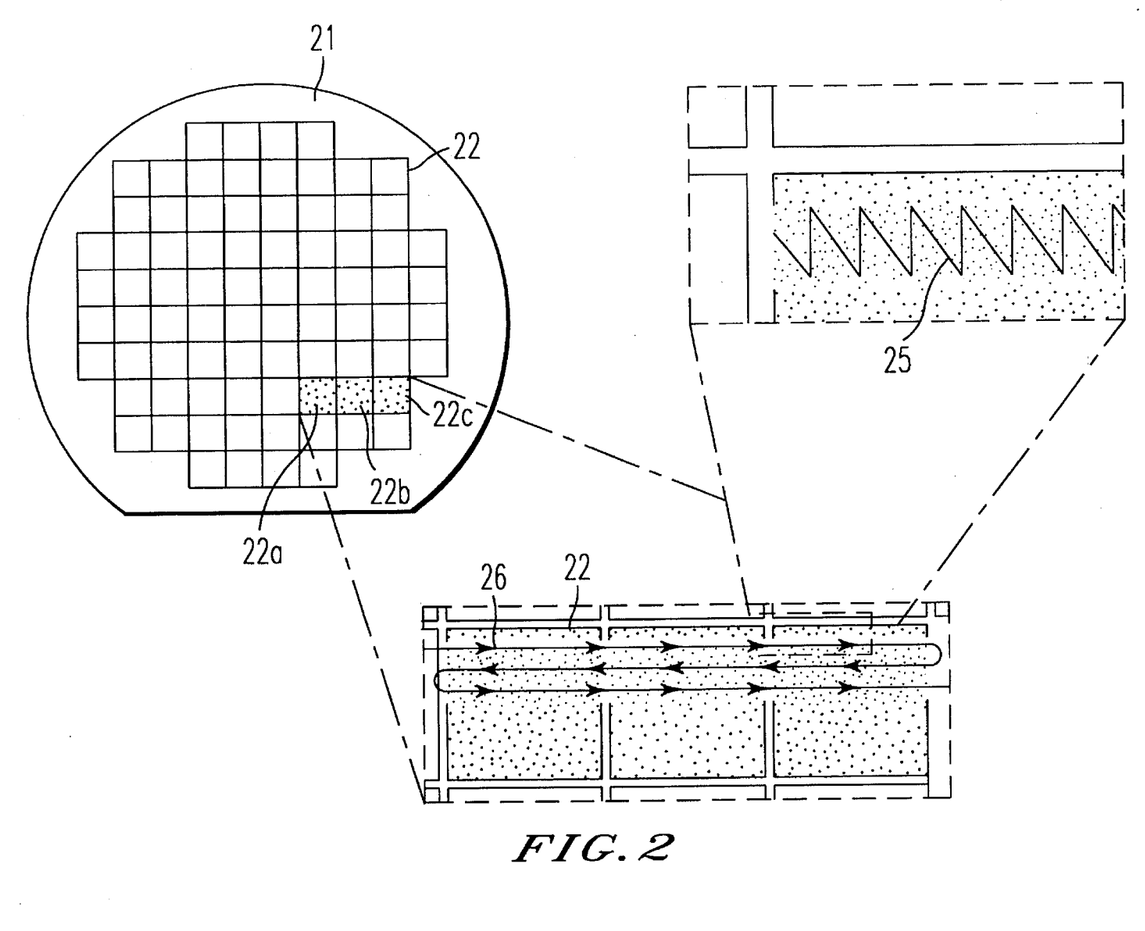
FIG. 2 is a drawing which shows the method of scanning the beam over the wafer surface in an image-comparison type of defect inspection apparatus.

FIG. 1 and FIG. 2 show the shape of the beam and the scanning method in the defect detection method of the prior art. First, a circular beam 11, which has a finite size (beam diameter R) is raster-scanned in the X direction as a stage is moved in the Y direction. As a result, the pattern on the wafer surface 21 are scanned in rectangular strips.

In doing this, as shown in FIG. 2, a specific chip 22 on the wafer surface 21 is scanned by the beam 11. This example is that of three chips, 22a through 22c, to be inspected, these being scanned together. That is, by moving the stage in the Y direction while scanning the beam in the X direction, the beam is moved through the sawtooth path having the desired width, which is shown by the arrow line 25, thereby scanning over a rectangular strip. The scanned region covered on the overall chip in a back-and-forth movement as shown by the arrow line 26, thereby enabling the scanning of the entire chip surface.

The beam diameter R is required to be 0.1 µm if the required defect detection sensitivity is 0.1 µm. A signal which is synchronized to the raster scanning of the beam 11 is output every pitch $\Delta X$, that is, every 0.1 µm in this example, and this signal captures one pixel, which an image is formed. If we assume that 100% of the surface of the wafer 21 is to be covered, with no skipped areas, the Y-direction pitch $\Delta Y$ is also established by the beam diameter R, and in this example this 0.1 µm. In FIG. 1, X1, X2, ..., XN are the X-axis addresses on the stage corresponding to each pixel (the X-direction position of the center of the beam), while Y1, Y2, ..., YN are the Y-axis addresses on the stage corresponding to each pixel (the Y-direction position of the center of the beam). An image processor performs the above-described comparison of pairs of signals corresponding to pixels to extract defects.

In the above scheme, the time required for scanning is established by the beam diameter R which is required to achieve the desired inspection sensitivity (and the scanning pitch which this establishes) and the S/N ratio of the signal captured at the pixel 14.

The above-noted S/N is established by the amount of current in the incident electron beam. Therefore, in the defect detection method of the prior art as described above, by making the beam current large, it is possible to detect defects with a sufficiently high contrast.

However, for the following reason, the amount of beam current is limited. Specifically, the object being observed is the pattern formed on the wafer surface and because, as is well known, most of the pattern formed on the wafer surface consists of insulating material, it is necessary to prevent an electrical charge from developing on this insulating material during observation. More specifically, observation is performed at small energy levels of 1 keV or lower. Because of the low primary electron energy, the aberration characteristics of the lens deteriorates, and there is a serious problem with a drop in the S/N ratio (lowering of contrast) caused by the decrease in the injected number of electrons.

To avoid this problem and maintain the maximum detection sensitivity, it is desirable to either make the scanning of the beam slow, so that the amount of time the beam, which corresponds to a pixel, remains in one position is lengthened, thereby increasing the number of injected electrons per pixel, or to scan a given single pixel repeatedly, performing accumulation processing to improve the S/N ratio. In either case, however, the result is that the inspection time is greatly increased.

SUMMARY OF THE INVENTION

In consideration of the problems associated with the above-noted prior art, the present invention has as an object the provision of a wafer pattern defect detection method and apparatus therefor, which is capable of performing inspection with enhanced speed, without sacrificing defect detection sensitivity.

Another object of the present invention is to scan a wafer pattern by means of a rectangular electron beam.

Yet another object of the present invention is the generation of a rectangular electron beam, with a uniform amount of light density and without wasting any amount of light from the light source.

A wafer pattern defect detection apparatus according to the present invention has a rectangular electron beam generation means for scanning a rectangular electron beam from a rectangular light source which is of a size adjusted for the size of the pattern on the wafer under inspection so as to scan the part of the wafer to be inspected, electron signal detection means for detecting an electron signal which is generated from the above-noted wafer under inspection, and defect detection means for detecting the presence of a defect in the above-noted wafer under inspection, by means of electron signal image data which is based on the output signal from the above-noted electron signal detection means.

The rectangular electron beam generation means can be configured so as to have an electrostatic lens which deflects the rectangular electron beam from the light source and focuses it onto the pattern to be inspected of the wafer under inspection.

The electron signal detection means can be configured as a reflected electron signal detection means which detects an electron signal reflected from the wafer under inspection or as a secondary electron signal detection means which detects secondary electrons from the surface of the wafer under inspection.

The secondary electron detection means has a secondary electron detecting sensor and an electrostatic lens which forms an image of the secondary electron signal from the surface of the wafer under inspection on the image plane of the above-noted secondary electron detecting sensor.

The secondary electron detecting sensor can be configured so as to have a multi-anode electrode which is divided into a number of sections, and a microchannel plate device which guides secondary electrons from the surface of the wafer under inspection to the multi-anode electrode.

The secondary electron detecting sensor has a microchannel plate device that has a three-stage microchannel plate.

The secondary electron detecting sensor has a linear image sensor and a microchannel plate device which guides secondary electrons from the surface of the wafer under inspection to the above-noted linear image sensor.

The microchannel plate device can be configured so as to have a two-stage microchannel plate, a received image section having a phosphor surface onto which is formed a image of the output signal from the above-noted two-stage microchannel plate, and an optical fiber which guides the signal from the above-noted received image section to a linear image sensor.

The defect detection means can be configured so that it performs a comparison of the secondary electron images from the same regions on the surface of the wafer under inspection and another wafer which has formed on it the same pattern, and so that it makes a determination of the existence or non-existence of a defect on the surface of the wafer under inspection by means of determining whether or not the patterns are the same.

It is desirable that the defect detection means have a function which, when the two secondary electron image data are not the same, performs a comparison between those two secondary electron image data and another secondary electron image data that has the same pattern, and if the result is that they are not the same, judges the pattern to have a defect.

A wafer pattern defect detection method according to the present invention has a step of outputting a rectangular electron beam from a rectangular light source, a step of scanning the surface of a wafer under inspection by means of the above-noted rectangular electron beam and detecting the seconding electron signal from the surface of the wafer under inspection, and a step of generating secondary electron image data from the above-noted secondary electron signal and detecting defects on the surface of the wafer under inspection from this secondary electron image data.

DESCRIPTION OF THE PREFERRED EMBODIMENTS

Figure 3:
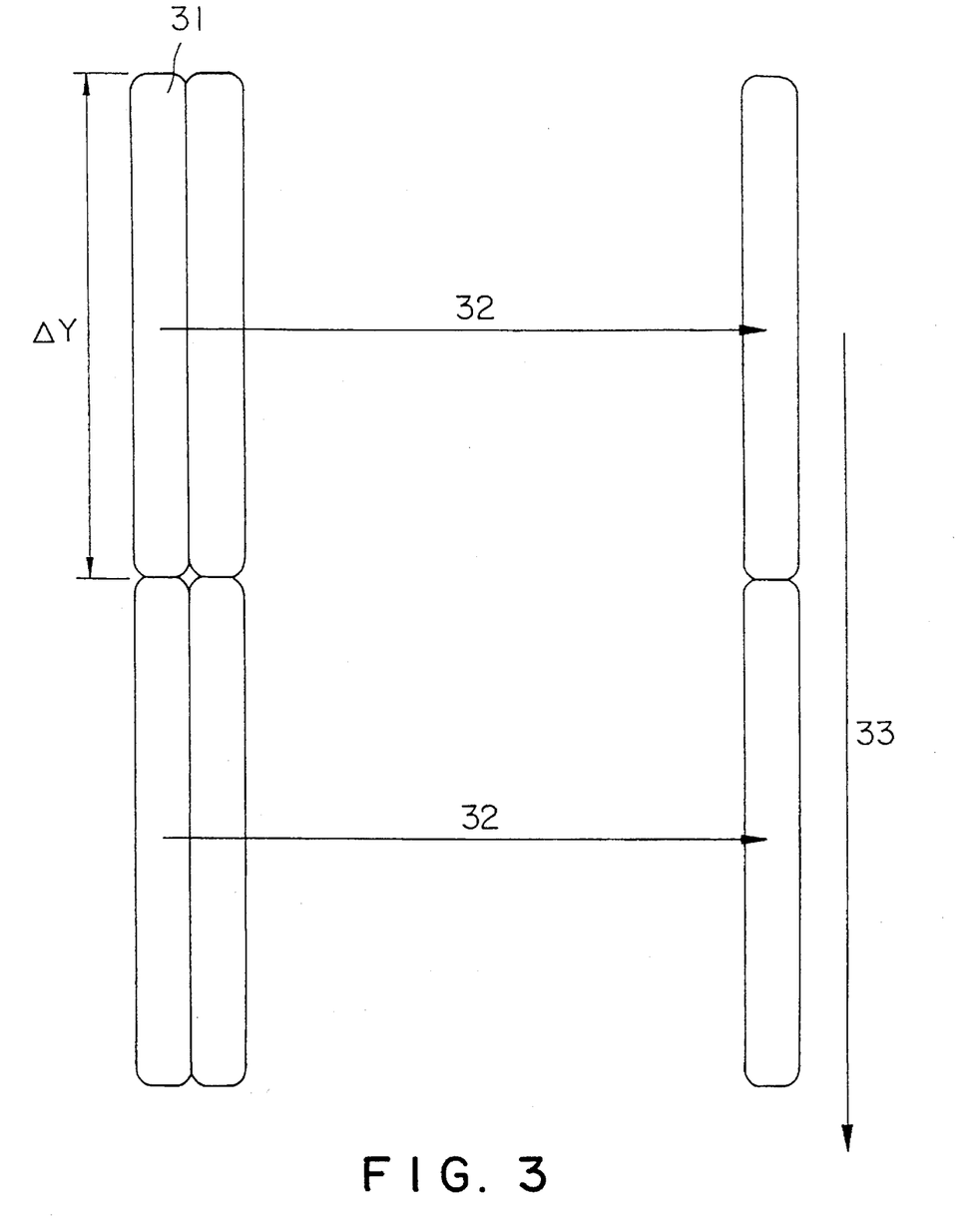
FIG. 3 is a drawing which shows the shape of the beam and the method of scanning the beam in the present invention.
Figure 4:
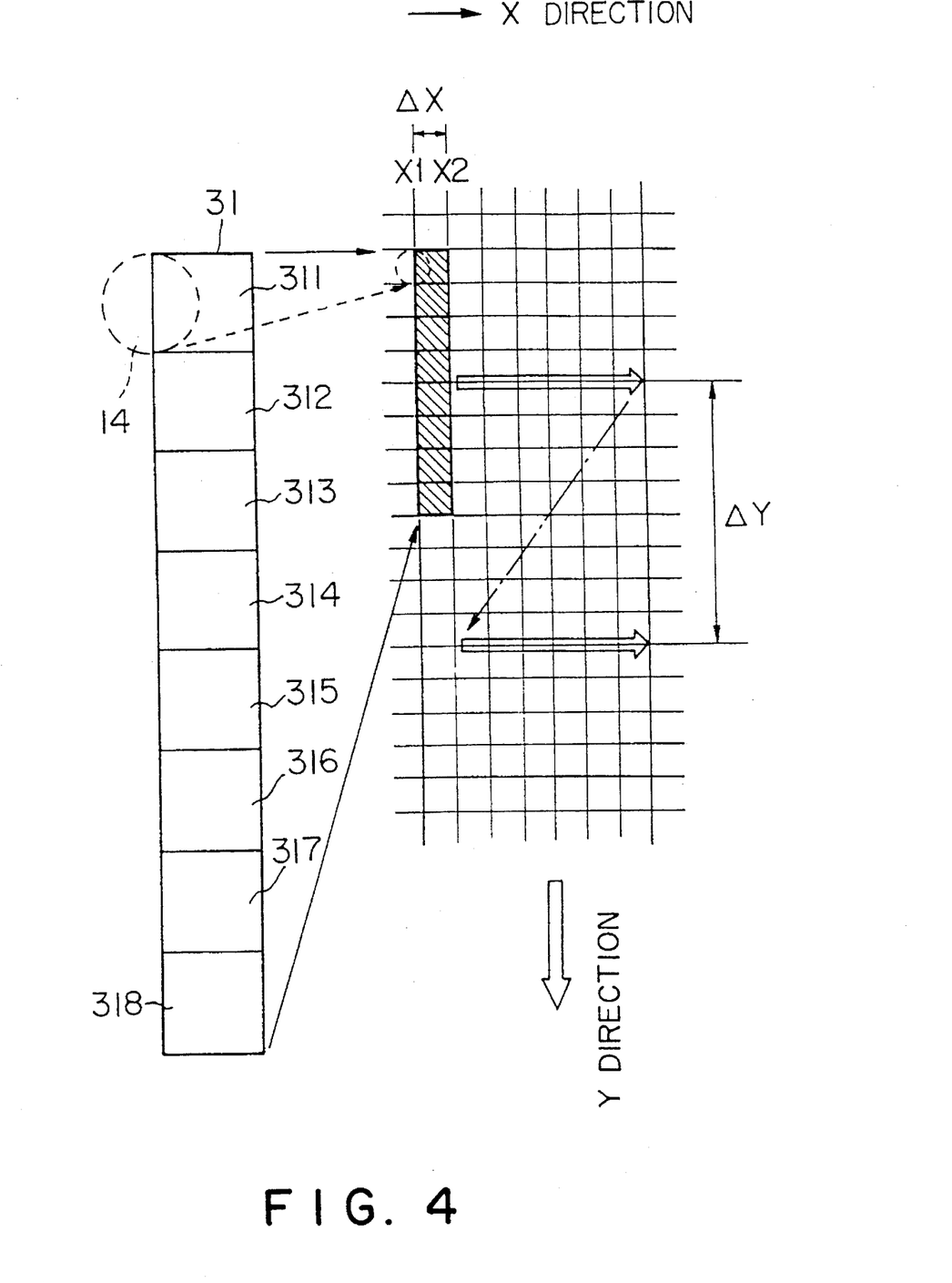
FIG. 4 is a drawing which shows the relationship of the shape of the beam and the scanning method in the present invention to the wafer pattern.

FIG. 3 shows the shape of the beam and the method of scanning the beam in the present invention, while FIG. 4 shows the relationship of the shape of the beam and the method of scanning the beam to the wafer pattern. As shown in FIG. 3, electron beam 31 is formed as a rectangular beam, this rectangular electron beam 31 being raster-scanned over the surface of the wafer under inspection. In doing this, a deflector is used to scan the electron beam 31 in the short-axis direction indicated by the arrows 32, as the stage is moved in the long-axis direction (Y direction) indicated by the arrow 33 at the same pitch as the long-axis length of the beam, ΔY, thereby causing the electron beam to be scanned across the surface of the wafer under inspection. In the case of the rectangular electron beam 31 shown in FIG. 4, a comparison with the circular electron beam 14 used in the prior art shows that the electron beams 14 and 31 have the same dimension in the X direction, but that the electron beam 31 has a Y-direction dimension that is 8 times that of the prior art circular beam, so that the Y-direction pitch is 8 times that of the prior art. Thus, the XY scan speed is also 8 times that of the prior art scanning, and if we consider that the X-direction speed is the same as the prior art, it can be seen that while the scanning speed is high, the sensitivity is the same as the prior art.

Specifically, if the circular electron beam 14 of the prior art were to be rectangular in shape, the rectangular electron beam 31 of this embodiment would correspond to the case of eight of such beams lined up in the Y direction, so that in this embodiment an area requiring eight direction reversals in the Y direction with the prior art is covered by just one direction reversal, thereby improving the scanning speed without a decrease in sensitivity.

Figure 5A:
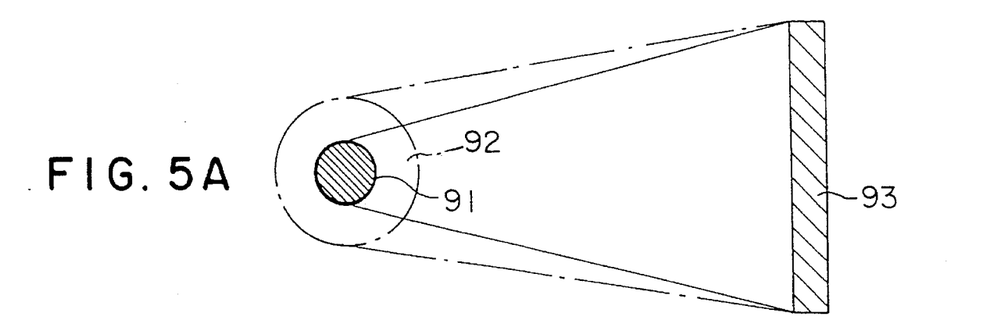
FIGS. 5A through 5C are drawings which show a comparison of the light source of the present invention with that of the prior art.
Figure 5B:
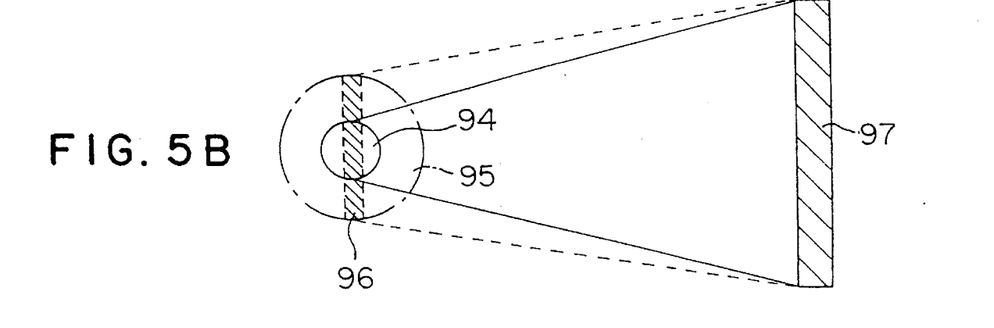
Figure 5C:
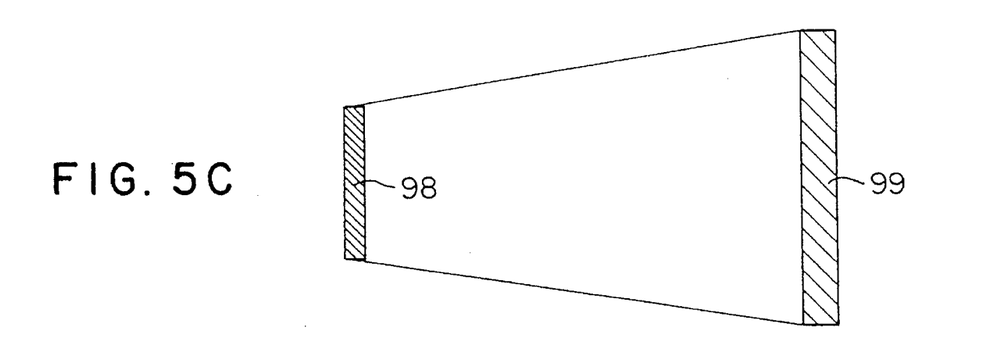

Technologies that can be used to obtain a rectangular electron beam include the three technologies shown in FIGS. 5A through 5C. FIG. 5A shows the deformation of a circular electron beam into a rectangular shape by means of the electric field of an electron beam generator, and in this case the X-direction and Y-direction deflection of the electron beam are controlled by adjusting the electric field of the lens to change its shape from circular to rectangular. It is difficult to control the electric field of the lens so that the amount of light is uniform over a cross-section of the beam viewed locally.

FIG. 5B shows the method of obtaining a rectangular electron beam by passing a circular electron beam through a slit. In this case, since the parts of the circular beam not needed in the rectangular electron beam are eliminated, these parts of the circular electron beam are wasted.

FIG. 5C shows the method used in the present invention to obtain a rectangular electron beam from a rectangular light source. In the case of the present invention, in which the electron beam from a light source is made rectangular, the control of the electric field of the lens is not difficult, as in the case shown in FIG. 5A, nor is there waste of the output of the light source as there is in the case of FIG. 5B.

One method known in the past as a technology for forming a rectangular beam is that of using a multiplepole lens (a quadrupole lens in the embodiment) to form a point light source into a rectangular image, the length (aspect ratio) and current density distribution of this image being controlled by changing the excitation conditions of the quadrupole lens (disclosed by Okayama and Tsurushima in unexamined patent application publication Sho 60-233814 (examined patent application publication Hei 2-49533)). In this method, because a quadrupole lens, which is an asymmetrical lens, is used to broaden the point light source to form the beam, the maximum total current of the beam thus obtained is limited by the amount of current emitted from the cathode. Therefore, if the aspect ratio is made large, a problem of a decrease in the current density to the extent that the cross-sectional area is increased occurs.

Because a reduction in the current density causes a reduction in the amount of signal obtained per unit surface area (within one pixel), as a result the scan time increases as the S/N ratio decreases. In consideration of the shortening of the scan time, which is the ultimate object of the present invention, this method is unsuitable.

Brodie (Brodie. J. Vac. Technol. B8, p. 1691, 1990) proposed a method of using a rectangular cathode and a doublet or triplet electrostatic quadrupole lens to form a rectangular beam with an aspect ratio that can be varied and also of converging this rectangular beam using converging optics consisting of a conventional condensing lens and objective lens. However, with the operating conditions of this quadrupole lens system, because the excitation conditions are low, the demagnification ratio is small, and for this reason the quadrupole lens system is used only as a probe forming lens, an electromagnetic condenser lens and objective lens being added as a demagnification system, thus achieving a larger demagnification ratio. The result of this approach is to make the electro-optical system complex, so that the overall configuration is large and heavy.

In this proposal, the electro-optical system formed by the indicated rectangular cathode and quadrupole lens:

(1) performs arbitrary independent control of the demagnification ratio Mx of the circular beam (aspect ratio: 1) and the rectangular beam (aspect ratio: N) in the length direction, and does so without a decrease in the current density, and (2) is capable of forming a microbeam with only an electromagnetic quadrupole lens system, without the need for supplementary lens systems such as an electrostatic lens type demagnifying optics system.

By scanning with a rectangular beam, because the scanning pitch in the long axis (Y direction) is the same as the length in the direction of this long axis, there is a great reduction in the time required to perform a scan of the surface of the wafer under inspection. For example, with a rectangular beam having an aspect ratio of N=10, the scanning time is 1/N, so that it is reduced to 1/10. However, while this enables the achievement of defect detection resolution, the Y direction, which is the long-axis direction, exhibits a decrease in resolution to the extent of the aspect ratio. To compensate for this, in the present invention a magnifying projection type secondary electron detection system is employed to prevent the decrease in the spatial resolution in the Y-axis direction.

Figure 6:
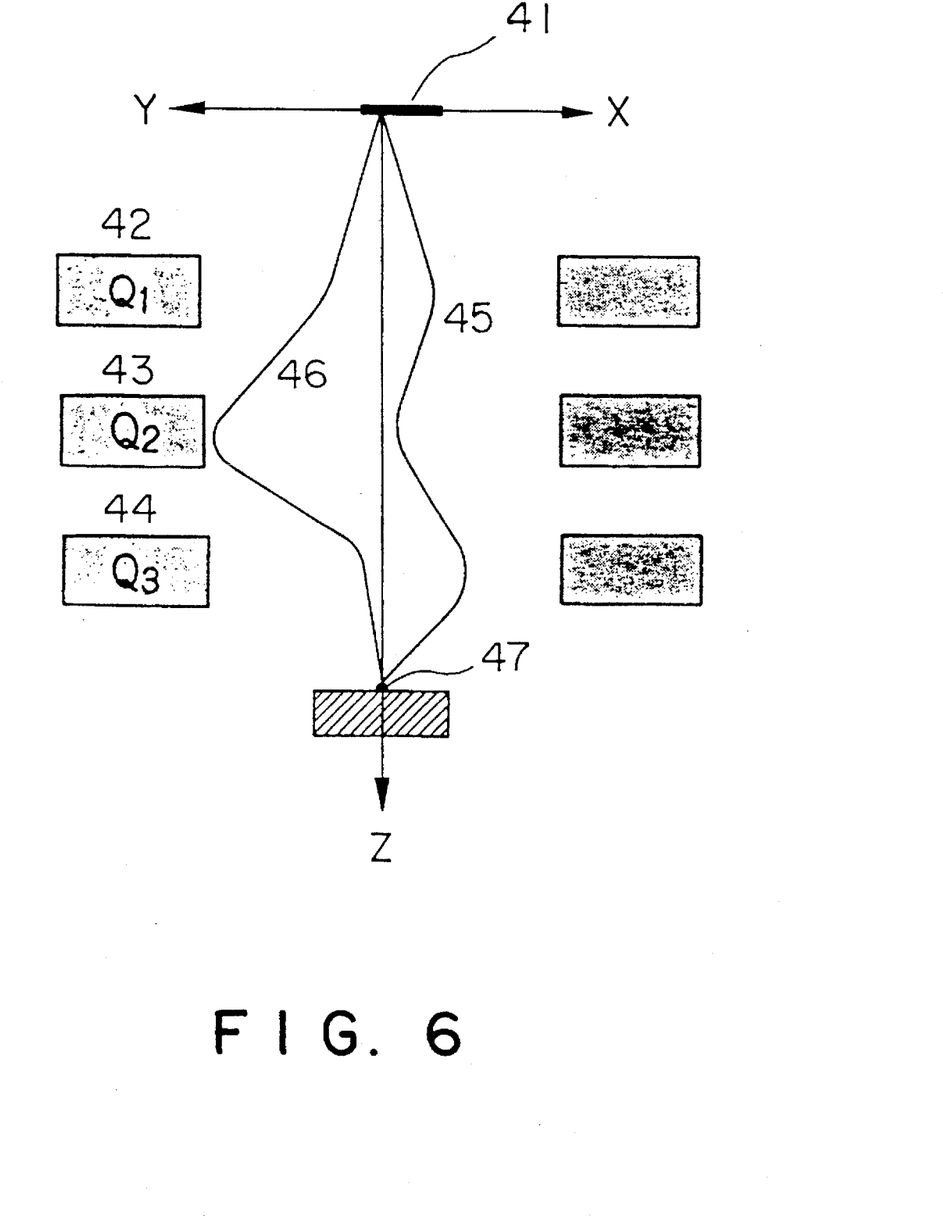
FIG. 6 is a drawing which shows the basic configuration of the electro-optical system of the rectangular cathode and quadrupole lens in the column present invention.

FIG. 6 shows an optical system which generates a rectangular electron beam, such as is shown in FIG. 5C. In this drawing, with the long-axis direction of the rectangular cathode taken as the X axis and the short-axis direction of this cathode taken as the Y axis, an example of an X trajectory shown as 45 (the trajectory of an electron emitted in the long-axis direction cross-section of the cathode) and of a Y trajectory shown as 46 (the trajectory of an electron emitted in the short-axis direction cross-section of the cathode) are shown. These two trajectories intersect at the image plane 47 on the Z axis, and the image of the cathode 44 is formed at the image plane at this position. If the value of ratio Mx/My of the X-axis magnification (demagnification) Mx to the Y-axis magnification (demagnification) coincides with the aspect ratio of the rectangular cathode 41 (ratio of length to width), there will be convergence at the image plane of 1:1, that is, convergence to a circular beam.

Under these conditions, by setting the long-axis direction magnification (demagnification) ratio Mx to a small value, the shape of the beam formed at the image plane 47 becomes a rectangle with its long-axis in the X-axis direction. For example, for a rectangular cathode measuring 100 μm by 10 μm, to obtain a circular beam having a diameter of 0.1 μm, it is necessary to have $Mx=10^{-3}$ and $My=10^{-2}$. However, by setting $Mx=10^{-2}$, it is possible to obtain a rectangular electron beam measuring 0.1 μm by 1 μm.

Figure 7:
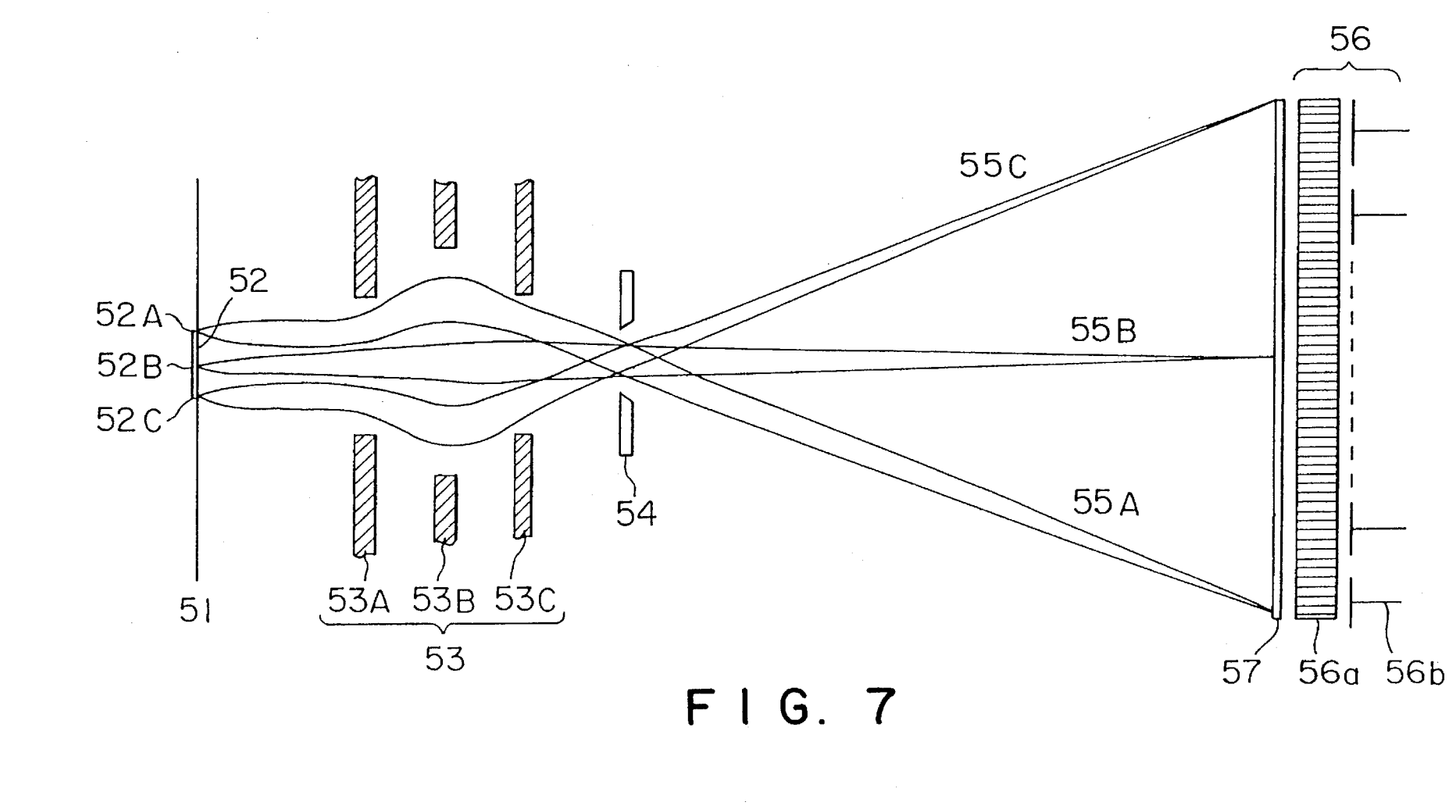
FIG. 7 is a drawing which shows the configuration of the secondary electron detection system of the present invention.
Figure 8:
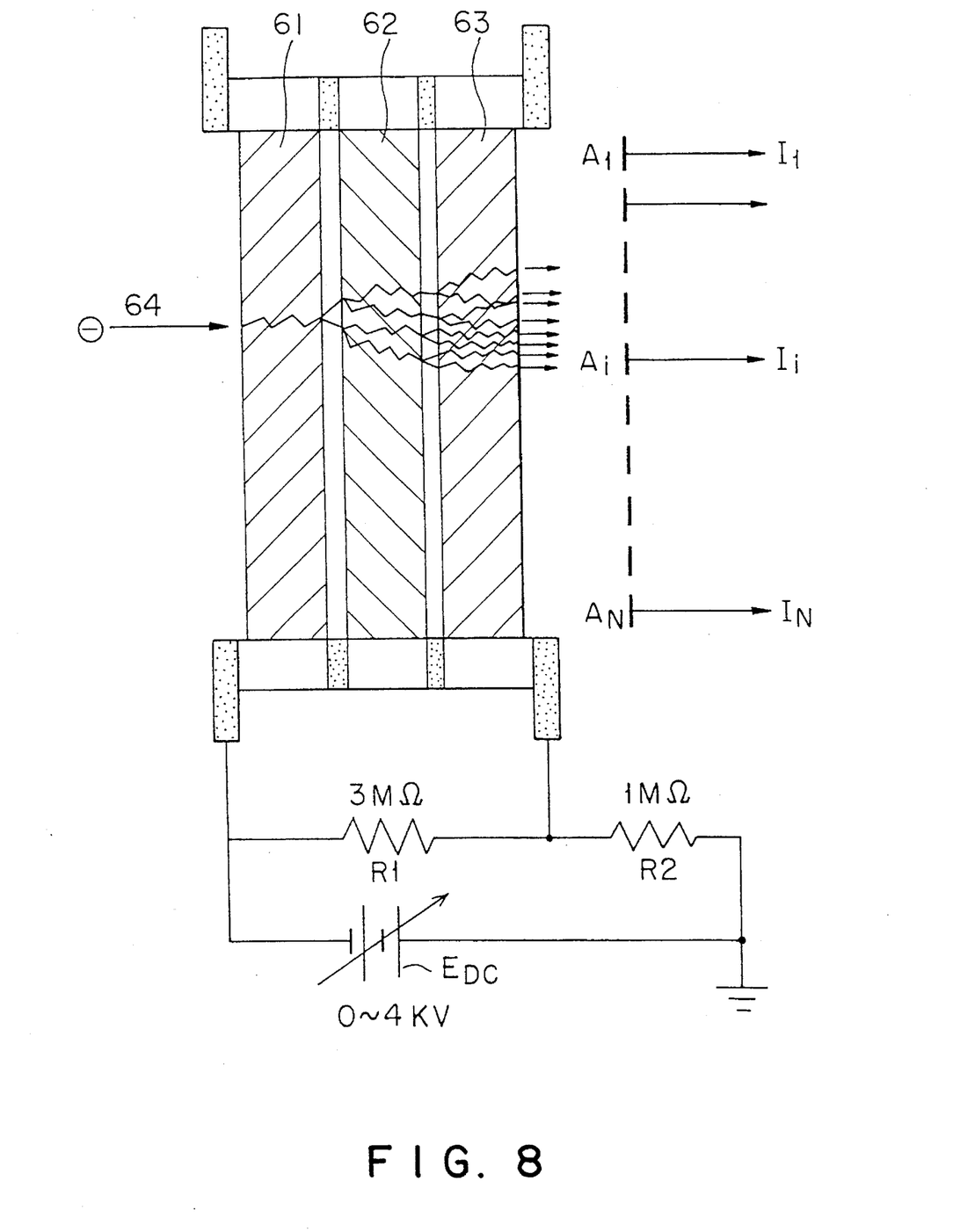
FIG. 8 is a drawing which shows the construction of a multi-anode-type microchannel plate (MCP).

Two major characteristics of the electro-optical system formed by the rectangular cathode and quadrupole lens (multipole lens) indicated herein are:

(1) because a rectangular cathode is used, the electron-emitting surface area is large, and because the beam trajectories intersect midway and the crossovers are brought together, it is possible to obtain a large current due to the reduction in the influence of the space charge effect, and (2) it is possible to easily form a rectangular beam by merely changing the X-axis direction magnification Mx and further it is possible to do so without a change occurring in the current density. FIG. 7 shows the basic configuration of an optical system which detects secondary electrons from the surface of the wafer under inspection. As shown in this drawing, this optical system is formed from the surface of the wafer under inspection 51, a rectangular cathode light source 52, an electrostatic lens 53, and a slit 54, with the rectangular cathode light source 52 positioned a Z=0, and the electron beam converged by a number of stages of electrostatic quadrupole lenses. In this drawing, which illustrates this embodiment of the present invention, this is a triplet which has the three stages of quadrupole lens 53a, 53b, and 53c. While the simplest quadrupole lens is shown in this example, a multipole lens system having an octupole lens or even a lens having more electrodes can also be used. In addition, if structural complexity is not a problem, a quartet which consists of four stages can also be used. The electron beam components 55A through 55C from the light source 52, which correspond to the pixels 52A, 52B, and 52C, intersect at the slit 54 and are formed as an image at the image plane 57. The beam which is formed at the image plane 57 is detected by means of a line-sensor type secondary electron detector 56. This secondary electron detector 56 is formed by the CCD sensor section 56a and the transfer electrodes 56b, an electrical charge responsive to the strength of the electron beam formed on the image plane 57 being accumulated in the CCD sensor section 56a, the charge thus accumulated in the CCD sensor section 56a being transferred to the outside by the transfer electrodes 56b, which each correspond to the variation positions. An actual example of a desirable secondary electron detector 56 would be a multi-anode MCP (microchannel plate). FIG. 8 shows the construction of this multi-anode MCP. A multi-anode MCP has a number of independent anodes lined up in a one-dimensional or two-dimensional arrangement. Because each of the anodes operates independently, it is possible to obtain position information which is dependent upon the anode positions. Because the measurement is performed at one time, it is possible to perform parallel readout, this providing the advantage of an expected increase in speed. Since in this embodiment of the present invention a single row of pixel information is read out from the rectangular beam, the drawing shows the simplest arrangement of cathodes, which is a single line of anodes arranged in one dimension. To achieve high sensitivity, a three-stage MCP, consisting of the first MCP 61, the second MCP 62, and the third MCP 63, is used, the three MCP plates being arranged in a straight line, and a power supply $E_{DC}$ being connected across the voltage divider formed by the resistors R1 and R2 which are connected between MCPs 61 to 63. By means of the above-described construction, secondary electrons 64 are successively multiplied by the three stages of MCPs, 61 to 63. The multiplied group of electrons are detected by the separated anode electrodes A1, . . . , Ai. . . . , AN, and are output as current signals I1, . . . , Ii. . . . , IN. In consideration of the influence of crosstalk (which manifests itself as a broadening of the group of multiplied secondary electrons during the multiplying process) the pitch of anodes A1, . . . , Ai . . . , AN should be set in the approximate range from 0.5 mm to several millimeters.

This pitch is established by the magnification ratio of the projection-type secondary electron detection system, and if we assume that the multiplying system multiplies and projects the secondary electrons from a 0.1-μm pixel by 5000 times, the ideal arrangement pitch would be 0.5 mm. If the aspect ratio is in the range of approximately 10 to 100, this multi-anode MCP is the most appropriate. If, however, the aspect ratio is made yet larger, the construction becomes complex.

Figure 9:
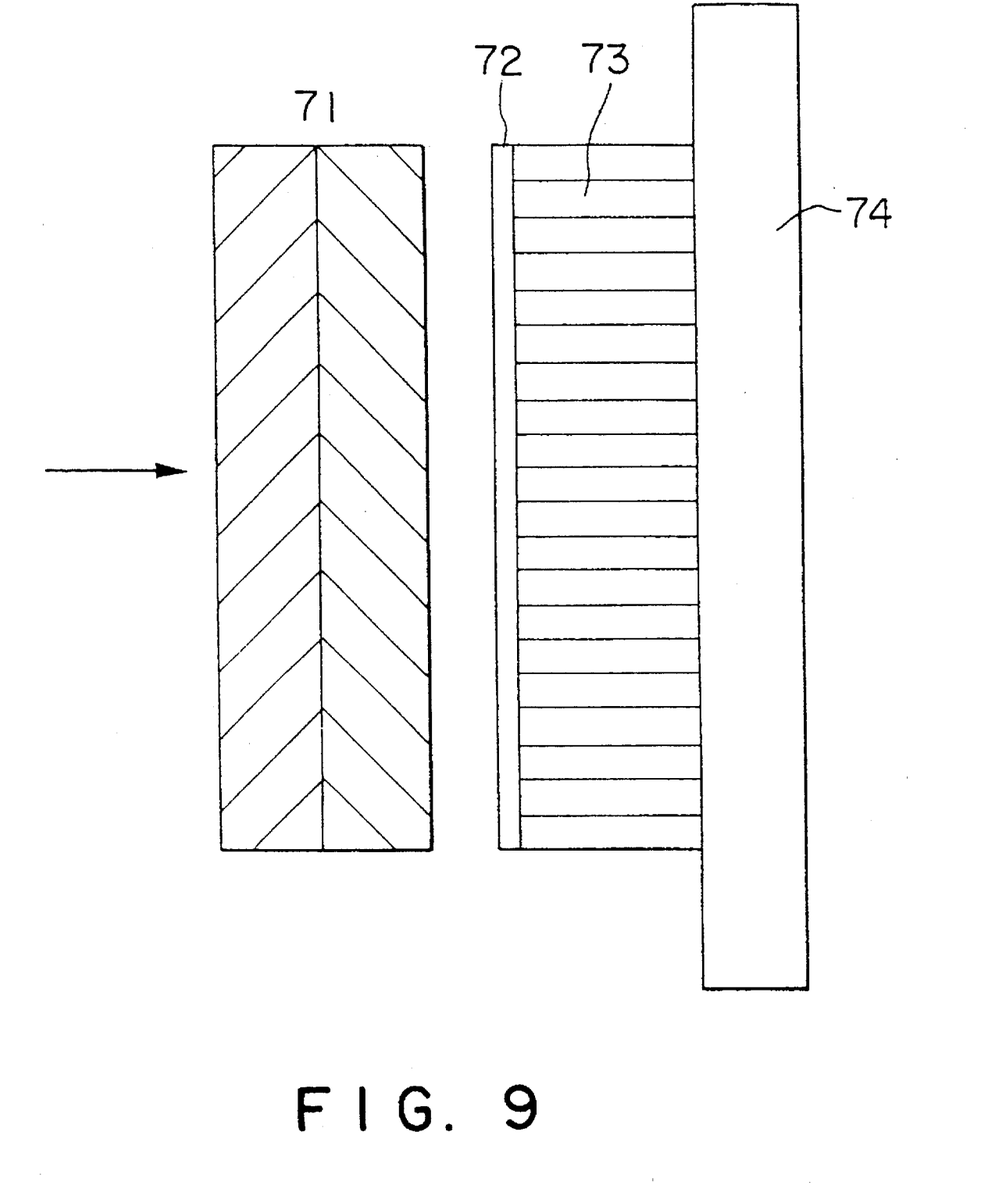
FIG. 9 is a drawing which shows the construction of a secondary electron detector which uses a linear image sensor.

If a complex construction presents problems, it is desirable to employ an MCP-phosphor surface-linear image sensor type of secondary electron detector. FIG. 9 shows the configuration of this type of secondary electron detector, this detector being formed by positioning at the last stage of MCP 71 (two-stage configuration in this embodiment) a fiber plate 73 onto which has been applied a phosphor surface 72, the signal of the multiplied electron group being converted into an optical signal, and this being converted to an electrical signal by means of the MOS-type linear image sensor 74.

A MOS-type linear image sensor is a self-scanning photodiode array, this having a scanning circuit formed by n-channel MOS transistors. The light-receiving surface area of each of the photodiodes is large, this being 50 μm by 2.5 mm or 25 μm by 2.5 mm and the noise level of such a sensor is extremely low. This image sensor consists of 512 or 1024 channels aligned in a row.

While this method can accommodate a high aspect ratio rectangular beam relatively easily, the signal readout is performed in serial fashion, and the clock frequency of the linear image sensor also presents limitations to the achievable speed. The ultimately achieved spatial resolution is established by the aberration of the projection type secondary electron detection system. This is because while the X-direction spatial resolution is established by the beam length in the short-axis direction (X axis) of the primary rectangular beam, there is broadening in the long-axis direction (Y axis) due to the influence of aberration in the projection-type secondary electron detection system. As a result, the signal for a single pixel is broadened to the extent of the aberration of the secondary electron detection system. Therefore, the thus-obtained Y-axis direction signal profile is distorted.

However, because it is clear that the distortion of this signal profile is due only to the aberration in the secondary electron detection system, it is correctable. The method for doing that is described below.

The broadening of the signal caused by aberration, in theory, exhibits a Gaussian distribution, with the amount of broadening being expressed as a diameter of $1/e^2$. This is the equivalent of performing the convolution (spatial filtering) using a Gaussian filter of a hypothetical signal having the ideal condition of no aberration (true secondary electron signal). That is, if the hypothetical secondary electron signal with no aberration is X and the detected secondary electron signal is Y, the convolution of the profile H, which is broadened by aberration, and the hypothetical true secondary electron signal X with no aberration is given by the following equation.

$$Y(i) = \sum_{j=-\infty}^{\infty} H(j) \cdot X(i-j)$$

Therefore, if the beam broadening determined by calculation or, more realistically, the broadening of the signal caused by the secondary electron detection system and obtained by measurement is formed into a function and processed by convolution, it is possible to determine the true secondary electron signal. One method of determining the broadening of the signal caused by the secondary electron detection system is to perform a measurement of the beam profile, using for example the well-known knife-edge method.

Figure 10:
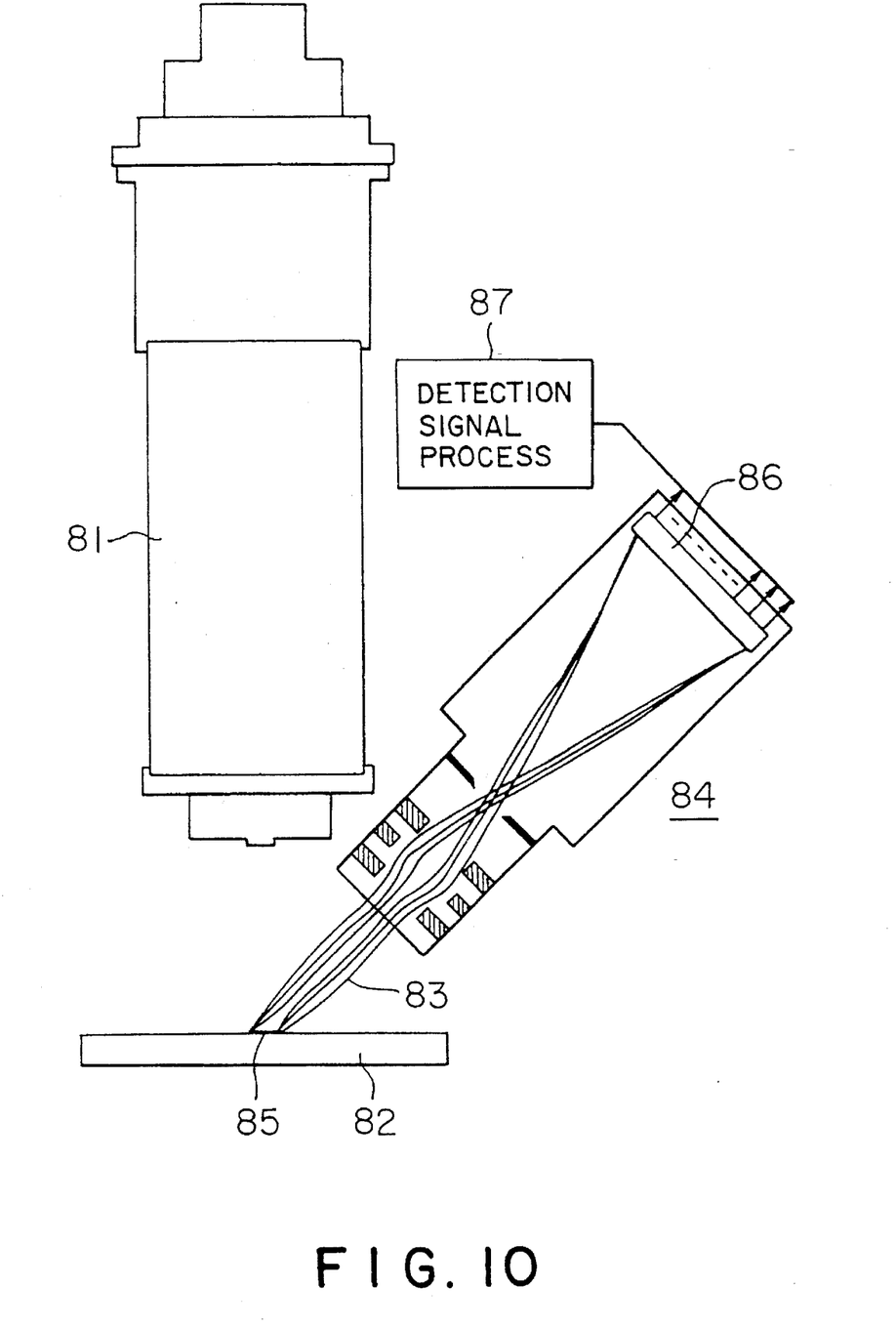
FIG. 10 is a drawing which shows the configuration of an inspection station block of a pattern defect inspection apparatus according to the present invention.

FIG. 10 is an overall view of a pattern defect detection apparatus of this embodiment of the present invention, in which 81 is an electro-optical system column, 82 is the wafer under inspection, 83 are secondary electrons, 84 is a secondary electron detection system, 85 is the image of the rectangular beam, and 86 is a line sensor type secondary electron detector. An optical system such as, for example, shown in FIG. 4, is located within the electro-optical system column 81, the output of this striking the surface of the wafer under inspection 82, and a secondary electron image 85 of the rectangular beam being formed. The secondary electron detection system 84 includes within it an optical system such as shown in FIG. 6, wherein, for example, the secondary electron image 85 of the wafer under inspection 82 is input at an angle of 45°, its intensity being detected by the line sensor type secondary electron detector 86. This detected signal is input to a detection signal processing circuit 87, A–D converted, and stored in internal memory. By means of this defect detection apparatus, an inspection is performed of a number wafers having the same pattern, a comparison being made of the data of the same regions on the wafers, agreement between the wafers being taken as a no-defect result, and a difference between the wafers being taken as a defect-found result. When a non-coincidence in patterns occurs, a comparison is made with, for example, another wafer having the same pattern, and similar processing is performed, a difference in patterns detected in the second comparison being taken as a defect-found result.

In the present invention as described above, a scanned electron beam is formed into a rectangular shape. An electro-optical system formed from a rectangular cathode and a quadrupole lens is most suitable for use in forming this rectangular beam. This rectangular beam is scanned by deflecting it in the short-axis direction of the rectangular beam (X-axis direction) while a stage is moved in the long-axis direction (Y-axis direction) at a pitch which is the same as the length of the beam in the long-axis direction, so that raster-scanning of the surface of the wafer under inspection is achieved. It is possible to consider the rectangular beam as the case in which a number of circular beams used in the prior art were lined up in the vertical direction. Therefore, if the beam horizontal movement direction for the rectangular beam is taken as the X direction and the vertical direction is taken as the Y direction, the X-direction size of the rectangular beam is the same as a circular beam and there is no loss of resolution. Therefore, in comparison with the prior art, the number of direction reversals in the Y direction is reduced, this bringing about in increase in the scanning speed. Because a number of pixel signals equal to the aspect ratio (ratio of the length in the long-axis direction to the length in the short-axis direction) the degree of the increase in scanning speed is the same as the aspect ratio of the rectangular beam. For this reason, if the current density of the rectangular beam is the same as that of a circular beam, the inspection time will be shortened to 1/(aspect ratio) with respect to the time required previously.

What is claimed is:

1. A wafer pattern defect detection apparatus, comprising:

rectangular electron beam generation means having a multipole electrostatic lens for generating a rectangular electron beam from a rectangular electron source, the rectangular electron beam being of a size adjusted for the size of the pattern on a wafer under inspection, the rectangular electron beam being focused, by the multipole electrostatic lens, on the part of the wafer to be inspected;

signal detecting means for detecting an electron signal which is generated from said wafer under inspection; and a defect detection means for detecting the presence of a defect inside wafer under inspection, by means of electron signal image data which is based on an output signal from said electron signal detection means.

2. A wafer pattern defect detection apparatus according to claim 1, wherein said electron signal detection means comprises electron signal detection means for detecting electrons reflected from the surface said wafer under inspection.

3. A wafer pattern defect detection apparatus according to claim 1, wherein said electron signal detection means comprises secondary electron signal detection means for detecting secondary electrons from the surface of said wafer under inspection.

4. A wafer pattern defect detection apparatus according to claim 3, wherein said secondary electron detection means comprises a secondary electron detecting sensor and an electrostatic-type lens which forms the electron signal from the surface of said wafer under inspection on an image plane of said secondary electron detecting sensor.

5. A wafer pattern defect detection apparatus according to claim 4, wherein said secondary electron detecting sensor comprises a multi-anode electrode divided into a plurality of sections and a microchannel plate device which guides secondary electrons from the surface of said wafer under inspection to said multi-anode electrode.

6. A wafer pattern defect detection apparatus according to claim 5, wherein said microchannel plate device comprises three stages of microchannel plates.

7. A wafer pattern defect detection apparatus according to claim 6, wherein said secondary electron detecting sensor comprises a linear image sensor and a microchannel plate device which guides secondary electrons from the surface of said wafer under inspection to said linear image sensor.

8. A wafer pattern defect detection apparatus according to claim 7, wherein said microchannel plate device comprises a two-stage microchannel plate, a image-receiving section which has a phosphor surface to form the image of the output signal of said two-stage microchannel plate, and an optical fiber which guides the signal from said image-receiving section.

9. A wafer pattern defect detection apparatus according to claim 1, wherein said defect detection means compares two secondary electron image data from the same regions of wafers under inspection that have the same pattern and detects the existence or non-existence of a defect by whether or not the two data coincide.

10. A wafer pattern defect detection apparatus according to claim 9, wherein when said two secondary electron image data do not coincide, said defect detection means compares each of these data to another secondary electron image data having the same pattern and, if the result is non-coincidence, judges the result to be a pattern defect.

11. A wafer pattern defect detection method comprising the steps of:

outputting a rectangular electron beam from a rectangular electron source;

focusing the rectangular electron beam by a multipole electrostatic lens on the surface of a wafer under inspection and detecting a secondary electron signal from the surface of the wafer under inspection; and generating secondary electron image data from said secondary electron signal and detecting defects on the surface of said wafer under inspection from said secondary electron image data.

* * * * *